United States Patent [19]

Gunge

[11] 4,418,150

[45] Nov. 29, 1983

[54] YEAST CONTAINING PLASMIDS PROVIDING KILLER CHARACTERISTICS

[75] Inventor: Norio Gunge, Ebina, Japan

[73] Assignee: Mitsubishi Chemical Industries Limited, Tokyo, Japan

[21] Appl. No.: 349,903

[22] Filed: Feb. 18, 1982

[30] Foreign Application Priority Data

Mar. 9, 1981 [JP] Japan ................................. 56-33453

[51] Int. Cl.$^3$ ....................... C12N 1/18; C12N 15/00; C12N 1/16
[52] U.S. Cl. ..................................... 435/256; 426/60; 426/62; 435/172; 435/255
[58] Field of Search ....................... 435/255, 256, 172; 426/60, 62

[56] References Cited

U.S. PATENT DOCUMENTS

| | | | |
|---|---|---|---|
| 3,930,956 | 1/1976 | Juni ................................. | 435/172 X |
| 4,172,764 | 10/1979 | Heslot et al. ........................ | 435/172 |
| 4,304,863 | 12/1981 | Collins et al. ....................... | 435/172 |
| 4,343,906 | 8/1972 | Reusser et al. .................. | 435/172 X |

OTHER PUBLICATIONS

Gunge, et al., Isolation and Characterization of Linear Droxyribonuleic Acid Plasmids from *Klayveromyces lactis* and the Plasmid–Associated Killer Character, J. of Bacteriology, Jan. 1981, vol. 145 (pp. 382-390).

Beggs, J. D. Transformation of Yeast by a Replicating Hybrid Plasmid, Nature, vol. 275 1978 (pp. 104-109).

Stewart, et al., The Genetic Manipulation of Industrial Yeast Strains, Current Developments in Yeast Research, Advances in Biotechnology, 1981 (pp. 17-24), Proceedings of the Fifth International Symposium on Yeasts, London; Canada Jul. 1980.

Wickner, R. B., "Killer Character" of *Saccharomyces cerevisiae:* Curing by Growth at Elevated Temperature, J. of Bacteriology 1974, vol. 117, No. 3 (pp. 1356-1357).

*Primary Examiner*—David M. Naff
*Attorney, Agent, or Firm*—Oblon, Fisher, Spivak, McClelland & Maier

[57] ABSTRACT

Killer yeasts having killer toxin-resistance and killer activity toward a wide range of types of yeasts are produced by introducing a certain plasmid into *Saccharomyces cerevisiae* by a cell fusion or transformation technique.

7 Claims, No Drawings

YEAST CONTAINING PLASMIDS PROVIDING KILLER CHARACTERISTICS

BACKGROUND OF THE INVENTION

Field of the Invention

The present invention relates to a killer yeast.

Sake yeasts having killer character are known to be useful for the prevention of contamination with wild yeasts encountered in the brewing of sake. That is, said killer sake yeasts are immune (resistant) to killer toxins, so the preparation and the use of excellent sake yeasts having killer activity has an advantage in that not only can they not be killed by wild killer yeasts mixed therewith but they also can prevent contamination with killer toxin-sensitive wild yeasts which are more often encountered. Judging from the viewpoint of finding a countermeasure against contamination with wild yeasts, such yeasts as are resistant to as many kinds of killer toxins (also referred to as killer substances) as possible produced by wild killer yeasts and have killer action toward as many kinds of wild yeasts as possible are preferred. The hitherto known killer strains of *Saccharomyces cerevisiae* are, however, not completely satisfactory in this point.

SUMMARY OF THE INVENTION

Upon extensive investigation, we, the inventors of the present invention, have found that a killer yeast having killer toxin-resistance and killer activity toward a wide range of types of yeasts are available by introducing a certain plasmid into *Saccharomyces cerevisiae* by a cell fusion or transformation technique. Thus, the present invention has been attained. Briefly, the essence of the present invention resides in *Saccharomyces cerevisiae* having resistance to killer toxins produced by killer strains of *Kluyveromyces lactis* and having the same killer character as said killer strains.

DETAILED DESCRIPTION OF THE PREFERRED EMBODIMENTS

The present invention will be explained in detail below.

The killer yeast according to the present invention belongs to *Saccharomyces cerevisiae* and has resistance to killer toxins produced by killer strains of *Kluyveromyces lactis* controlled by double-stranded DNA plasmids (pGK1-1 and PGK1-2) (for example, IFO 1267 strain or ATCC 8585 strain; here the IFO number is that designated by the Foundation Institute of Fermentation, Osaka to said strain deposited therewith and the ATCC number, is that given by American Type Culture Collection) and the same killer character as killer strains of *Kluyveromyces lactis*. The killer yeast according to the present invention has killer activity toward more kinds of yeasts as compared with the hitherto known killer strains of *Sacchararomyces cerevisiae* controlled by double-stranded RNA plasmids, for example, BO 60 (ATCC 42750) strain and B 511-4C (ATCC 38659) strain. That is, the killer yeast according to the present invention has, similarly with killer strains of *Kluyveromyces lactis*, for example, IFO 1267 strain, killer activity toward the following strains:

(1) Strains being subject to the killer activity (that is, those which are killed by the killer yeast according to the present invention):

| | |
|---|---|
| *Sacchararomyces cerevisiae* | G102D |
| | AH 22 (ATCC 38626) |
| | M1-7C |
| | BO 60 (killer strain) |
| | F38-4A killer (killer strain) |
| | B511-4C (killer strain) |
| *Kluyveromyces lactis* | IFO 1903 |
| | IFO 0433 |
| | L3d |
| | L4 |
| | L5 |
| *Kluyveromyces thermotolerans* | IFO 0662 |
| *Kluyveromyces vanudenii* | IFO 1673 |
| *Saccharomyces rouxii* | M1 |
| | M7 |
| *Torulopsis glabrata* | IFO 0005 |
| | IFO 0662 |
| *Candida utilis* | IFO 0396 |
| *Candida intermedia* | IFO 0761 |

(2) Strains being subject to the killer activity though to a lesser extent:

| | |
|---|---|
| *Saccharomyces italicus* | IFO 0523 |
| | IFO 1049 |
| *Kluyveromyces lactis* | W600B (ATCC 32143) |

The strains of the killer yeast according to the present invention as mentioned above include *Saccharomyces cerevisiae* F102-2 strain (deposited with the Agency of Industrial Science and Technology, the Fermentation Research Institute in Japan; the receipt number for the application for the deposit of the microorganism is 5903).

Further, the killer yeast according to the present invention may be defined to be one having resistance to killer toxins produced by killer strains of *Saccharomyces cerevisiae* (for example, BO60 strain) as well as to those produced by killer strains of Kluyveromyces lactis and having the same killer character as killer strains of *Saccharomyces cerevisiae* (for example, BO60 strain) as well as those of *Kluyveromyces lactis*. Here, therefore, the killer yeast according to the present invention is concluded to have the killer activity of both the killer strains of *Kluyveromyces lactis* and those of *Saccharomyces cerevisiae*. Concretely, the killer activity (in other words the death of strains due to the yeast according to the present invention) is found also in *Saccharomyces italicus* in addition to those strains as illustrated above. Further, the activity is usually enough in the case of *Saccharomyces italicus* IFO 0253 and 1049 strains among those strains as listed in 2) above as strains being subject to the activity though to a little extent.

The killer yeast according to the present invention is prepared by introducing plasmids found in a killer strain of *Kluyveromyces lactis* (pGK1-1 and pGK1-2 described in Journal of Bacteriology, vol. 145, pp. 382–390 (1981)) by a cell fusion or transformation technique.

A strain belonging to *Saccharomyces cerevisiae Hansen*, for example, AH22 (ATCC 38626) strain, BO60 (ATCC 42750) strain or the like, may be employed as the strain of *Saccharomyces cerevisiae* which becomes the acceptor for the plasmids. Particularly, a $\rho^{\circ}$ mutant namely mitochondrial DNA lacking strain is preferred to be employed. The use of BO60 strain or the like is preferred if it is intended to provide the killer yeast according to the present invention with resistance to killer strains of *Saccharomyces cerevisiae* and with the killer character of said killer strains. As the plasmids, there may be employed pGK1-1 and pGK1-2 found in killer strains of *Kluyveromyces lactis*, for example, IFO 1267 strain, as described in Journal of Bacteriology, vol. 145, pp. 382–390 (1981).

The pGK1-1 and pGK1-2 plasmids are linear DNA plasmids having the molecular weights of $5.4\pm0.1\times10^6$ daltons and $8.4\pm0.1\times10^6$ daltons, respectively, and the same density of 1.687 g/cm$^3$. The digestion properties of them with a variety kinds of restriction enzymes are as follows:

(1) pGK1-1:

| | |
|---|---|
| With EcoRI | digested into two fragments (m.w.: $2.4\times10^6$ and $3.0\times10^6$, the unit is dalton (the same will be applied hereunder)). |
| With HindIII | digested into three fragments ($0.5\times10^6$, $1.5\times10^6$ and $3.4\times10^6$). |
| With BglII | digested into three fragments ($4.0\times10^6$, $0.96\times10^6$ and $0.54\times10^6$). |
| With HincII | digested into two fragments ($4.1\times10^6$ and $1.4\times10^6$). |
| With PstI | digested into three fragments ($0.5\times10^6$, $1.0\times10^6$ and $3.9\times10^6$). |
| With BamHI | digested into two fragments ($2.7\times10^6$ and $2.7\times10^6$). |

With XhoI, HaeII, SmaI, SalI and HpaI: not digested.

(2) pGK1-2:

| | |
|---|---|
| With EcoRI | digested into seven fragments ($2.5\times10^6$, $2.3\times10^6$, $0.95\times10^6$, $0.85\times10^6$, $0.7\times10^6$, $0.55\times10^6$ and $0.5\times10^6$). |
| With BamHI | digested into two fragments ($3.6\times10^6$ and $4.8\times10^6$). |
| With HindIII, PstI, HpaI, XhoI, HaeII, SmaI and HincII | not digested. |

In order to construct the killer yeast according to the present invention, both the pGK1-1 and pGK1-2 are introduced into *Saccharomyces cerevisiae*.

When cell fusion is employed for the preparation of the killer yeast according to the present invention, in line with the conventional manner protoplasts from *Kluyveromyces lactis* harboring the above plasmids are mixed with those from *Saccharomyces cerevisiae*, and then the mixture is treated with polyethylene glycol. After this treatment the mixture is spread on an appropriate isotonic selective medium on which only protoplasts from *Saccharomyces cerevisiae* can be regenerated to obtain the object killer yeast.

In turn, if the preparation is effected by a transformation technique, conventionally the plasmids mentioned above are added to protoplasts from strains of *Saccharomyces cerevisiae* followed by the treatment with polyethylene glycol, and then the mixture was scattered in an isotonic medium. Then, strains having the killer function are isolated from colonies of regenerated protoplasts.

The killer yeast according to the present invention is obtained as mentioned above. In addition, also according to the present invention, useful proteinaceous products may be produced by introducing exogenous DNA (for example, genes coding for the production of human polypeptide hormones, enzymes, vaccine, etc.) into the above plasmids or a part of them (for example, a part in which the promotor, replication origin and killer factor portion are retained but from which other portions unnecessary for the plasmid replication or the expression of the introduced genes are removed) by the use of a recombinant DNA technique. Here, the killer activity is useful as the transformation maker.

Having generally described this invention, a more complete understanding can be obtained by reference to certain examples which are provided herein for purpose of illustration only and are not intended to be limiting in any manner.

EXAMPLE 1 (PREPARATION OF THE KILLER YEAST BY A CELL FUSION TECHNIQUE)

Protoplasts were prepared from each of 2 g of a killer strain of *Kluyveromyces lactis* designated as 2105-1D strain ($\alpha$ ade leu pGK1-1 and pGK1-2) (this strain is one of the tetrad spores obtained from the cross between *Kluyveromyces lactis* IFO 1267 strain and *Kluyveromyces lactis* W600B strain) and 0.8 g of a nonkiller strain of *Saccharomyces cerevisiae* designated as AH22 strain (a leu 2-3, leu 2-112 his 4-519 canl $\rho°$) and added to 10 and 5 ml of buffer solutions (0.1 M citrate-phosphate buffer solutions at pH 6.1), respectively to prepare suspensions. Two milliliters of the respective suspensions were taken to be mixed and subjected to centrifugation at 2,000 rpm for 10 min. To the resulting pellet there was added 4 ml of a 33% aqueous polyethylene glycol solution containing 50 mM of $CaCl_2$, and the mixture was subjected to incubation at 30° C. for 30 min. The mixture was centrifuged at 2,000 rpm for 10 min., and a 0.6 M KCl solution in water was added to the resulting pellet to prepare a suspension which was then poured on a NB (nitrogen base manufactured by Difco Laboratories)+leucine (leu)+histidine (his)+glucose medium (which contains 0.6 M KCl as the stabilizer), the medium for regeneration of the protoplasts from *Saccharomyces cerevisiae* AH22 strain. Many colonies were produced by incubation at 30° C. for about 5 days. From these, 243 colonies were separated and examined for the genetic markers and the killer character. Of 236 colonies having the same nucleic genetic markers as those of *Saccharomyces cerevisiae* AH22 strain (mating type a; requirements for leucine and histidine and resistance to canavanine (a leu 2-3, 2-112 his 4-519 canl)), 61 were found to have the killer character which is peculiar to *Kluyveromyces lactis* (properties of killing the killer strain B511-4C of *Saccharomyces cerevisiae*). By combined judgement of findings from tests by agarose gel analysis on whether the plasmids are harbored or not and other findings from taxonomic viewpoints including morphological features of cells and so on (for example, they were unable to assimilate lactose and were sensitive to cycloheximide), it is believed that the pGK1 plasmids transferred from *Kluyveromyces lactis* into *Saccharomyces cerevisiae* as a result of the cell fusion followed by the replication to develop the killer function. This strain is designated as *Saccharomyces cerevisiae* F102-2 strain (deposited with the Agency of Industrial Science and Technology, the Fermentation Research Institute under the receipt number 5903 for the application for the deposit of the microorganism).

EXAMPLE 2 (PREPARATION OF THE KILLER YEAST BY A TRANSFORMATION TECHNIQUE)

One gram of *Saccharomyces cerevisiae* AH22 strain (a leu 2-3, 2-112 his 4-519 canl $\rho°$) was converted to protoplasts which were washed with a 0.6 M KCl solution in water three times and centrifuged at 3,000 rpm for 10 min. The resulting pellet was suspended in 15 ml of a 10 mM Tris-hydrochloride buffer solution (containing 50 mM of $CaCl_2$ and 0.6 M of KCl). To 10 μl of the resulting suspension there was added 10 μl of a 3.6 M KCl solution in water followed by the addition of 40 μl of a 10 mM Tris-hydrochloride buffer solution at pH 7.6 containing 0.5 μg of pGK1-1 and 0.5 μg of pGK1-2 (the pGK1-1 and the pGK1-2 were prepared by the method described in Journal of Bacteriology, vol. 145, pp. 382-390) (which further contained 3 mM of EDTA). The resulting mixture (60 μl) was kept in ice bath for 30 min. followed by the addition of 500 μl of a 10 mM Tris-hydrochloride buffer solution (pH 7.6) containing a 40% polyethylene glycol (m.w.: 6,000), 50 mM of $CaCl_2$ and 0.6 M of KCl and then subjected to incubation at 30° C. for 60 min. while gently shaking. After the addition of a 0.6 M KCl solution in water, the mixture was spread on an isotonic YEPD medium and incubated at 30° C. for 4 days to obtain 6,000 colonies of protoplasts regenerated. From these colonies, 2,000 were isolated and examined for the killer function using *Saccharomyces cerevisiae* B511-4C strain as the tester. Of them, 2 colonies were transformed ones (killers). Subclones obtained by purification of these two transformed strains had the same genetic properties (a leu 2-3, 2-112 his 4-519 canl) and taxonomic properties (of being sensitive to cycloheximide and unable to assimilate lactose) as the parent AH22, and further showed the killer function of the killer strains of *Kluyveromyces lactis*. Also, any of the subclones harbored the pGK1 plasmids as determined by agarose gel analysis.

EXAMPLE 3 (PREPARATION OF THE KILLER YEAST BY A CELL FUSION TECHNIQUE)

Protoplasts were prepared from each of *Saccharomyces cerevisiae* having the killer character being peculiar to *Kluyveromyces lactis* and the killer BO60 strain of *Saccharomyces cerevisiae* and subjected to cell fusion on the basis of the cell fusion technique described in Example 1. Here, the nuclear fusion and the cytoplasmic mixing were caused at the same time, and the resulting *Saccharomyces cerevisiae* had the killer character of both *Kluyveromyces lactis* and *Saccharomyces cerevisiae* BO60 strain.

EXAMPLE 4 (DETERMINATION OF THE KILLER ACTIVITY)

The determination of the killer activity was carried out by the methylene blue agar technique described in Journal of Bacteriology, vol. 145, pp. 382-390. Cells of a tester strain (the strain to be tested for whether it is killed or not) were incubated in the YEPD medium (1% yeast extract+2% peptone+2% glucose). Then, the strain was suspended in sterile water, and 0.1 ml of ($10^7$ cells/ml) of the resulting suspension was spread on a killer assay medium (1% yeast extract+2% peptone+2% glucose+0.003% methylene blue+2.5% agar+0.05 M citrate-phosphate buffer at pH 5.0).

For the examination of the killer activity, cells of a strain of the killer yeast (the strain to be tested for whether it has killing ability) grown on YEPD agar were streaked onto the assay medium prepared as mentioned above on which the cells of the tester strain had been spread and incubated at 25° C. for 2-3 days. A clear killing zone is observed around the killer yeast if it has killer activity. In Table 1, the results are reported on the basis of the following criteria:

+: killing; −: nonkilling; and ±: weak killing—that is, a little killing zone was present around the killer yeast.

The results of the determination of the killer activity of the killer yeasts according to the present invention prepared in Examples 1-3 using the tester strains as listed in Table 1 are shown in the same table. In addition to them, also the killer activity of the killer strains of *Saccharomyces cerevisiae* (BO60 and B511-4C) and the killer strain of *Kluyveromyces lactis* (IFO 1267) is shown in Table 1.

TABLE 1

| Tester strains | Example 1 | Example 2 | Example 3 | S. cerevisiae BO60 and B511-4C *1 | K. lactis IFO 1267 *2 |
|---|---|---|---|---|---|
| *S. cerevisiae* | | | | | |
| G102D | + | + | + | + | + |
| M1-7C | + | + | + | + | + |
| BO60 | + | + | + | + | + |
| F38-4A | + | + | + | − | + |
| B511-4C | + | + | + | − | + |
| AH22 | + | + | + | + | + |
| *S. italicus* | | | | | |
| IFO 0253 | ± | ± | + | + | ± |
| IFO 0725 | − | − | + | + | − |
| IFO 1049 | ± | ± | + | + | ± |
| *K. lactis* | | | | | |
| IFO 1903 | + | + | + | − | + |
| K43 | − | − | − | − | − |
| L3α | + | + | + | − | + |
| WM37 | − | − | − | − | − |
| W600B | ± | ± | ± | − | ± |
| K51 | − | − | − | − | − |
| L4 | + | + | + | − | + |
| L5 | + | + | + | − | + |
| IFO 0648 | − | − | − | − | − |
| IFO 1090 | − | − | − | − | − |
| IFO 1267 | − | − | − | − | − |
| *K. thermotolerans* | | | | | |
| IFO 0662 | + | + | + | − | + |
| IFO 1050 | − | − | − | − | − |
| IFO 1674 | − | − | − | − | − |
| IFO 1778 | − | − | − | − | − |
| IFO 1779 | − | − | − | − | − |
| IFO 1780 | − | − | − | − | − |
| *K. africanus* | | | | | |
| IFO 1671 | − | − | − | − | − |
| *K. drosophilarum* | | | | | |
| IFO 1012 | − | − | − | − | − |
| *K. marxianus* | | | | | |
| IFO 0219 | − | − | − | − | − |
| *K. phaffi* | | | | | |
| IFO 1672 | − | − | − | − | − |
| *K. polysporus* | | | | | |
| IFO 0996 | − | − | − | − | − |
| *K. vanudenii* | | | | | |
| IFO 1673 | + | + | + | − | + |
| *K. wickerhamii* | | | | | |
| IFO 1675 | − | − | − | − | − |
| Schizosaccharomyces pombe | | | | | |
| M210 | − | − | − | − | − |
| SG55 | − | − | − | − | − |
| M216 | − | − | − | − | − |
| Killer yeast of Ex. 1 | | | | + | − |
| Killer yeast of Ex. 2 | | | | + | − |
| Killer yeast of Ex. 3 | | | | − | − |
| *S. rouxii* | | | | | |
| M1 | + | + | + | − | + |
| M7 | + | + | + | − | + |
| *Torulopsis glabrata* | | | | | |
| IFO 0005 | + | + | + | + | + |
| IFO 0662 | + | + | + | + | + |

TABLE 1-continued

| Tester strains | Example 1 | Example 2 | Example 3 | S. cerevisiae BO60 and B511-4C *1 | K. lactis IFO 1267 *2 |
|---|---|---|---|---|---|
| *Candida utilis* | | | | | |
| IFO 0396 | + | + | + | − | + |
| *Candida intermedia* | | | | | |
| IFO 0761 | + | + | + | − | + |

*1: BO60 strain and B511C strain showed completely the same killer acitivity, so they are listed in the same column. S. stands for Saccharomyces.
*2: K. stands for Kluyveromyces.

As is apparent from Table 1, the killer yeasts prepared in Examples 1 and 2 have the killer character of and resistance to *K. lactis* IFO 1267 strain. Further, the killer yeast prepared in Example 3 had the killer character of both *K. lactis* IFO 1267 strain and *S. cerevisiae* BO60 strain (or B511C strain) and resistance to the two strains.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A *Saccharomyces cerevisiae* yeast strain obtained by incorporating plasmids pGK1-1 and pGK1-2 into a nonkiller *Saccharomyces cerevisiae* yeast strain, said plasmids being obtained from a killer *Kluyveromyces lactis* strain, whereby said obtained *Saccharomyces cerevisiae* yeast strain exhibits the killer character of said killer *Kluyveromyces lactis* strain.

2. The yeast of claim 1, wherein said plasmids are obtained from *Kluyveromyces lactis* IFO 1267 or ATCC 8585.

3. The yeast of claim 1 wherein said yeast is *Saccharomyces cerevisiae* F 102-2 (FERM-P5903).

4. A *Saccharomyces cerevisiae* yeast strain obtained by incorporating plasmids PGK1-1 and PGK1-2 into a killer *Saccharomyces cerevisiae* yeast strain, said plasmids being obtained from a killer *Kluyveromyces lactis* strain, whereby said obtained *Saccharomyces cerevisiae* yeast strain has the killer character of said killer *Saccharomyces cerevisiae* yeast strain and of said *Kluyveromyces lactis* strain.

5. The yeast of claim 4, wherein said plasmids are obtained from *Kluyveromyces lactis* IFO 1267 or ATCC 8585.

6. The yeast of claim 4, wherein said killer strain is *Saccharomyces cerevisiae* BO 60 (ATCC 42750) or B 511-4C (ATCC 38659).

7. The yeast of claim 6, wherein said plasmids are obtained from *Kluyveromyces lactis* IFO 1267 or ATCC 8585.

* * * * *